US 6,690,452 B2

(12) United States Patent
Wilks, Jr.

(10) Patent No.: US 6,690,452 B2
(45) Date of Patent: Feb. 10, 2004

(54) MONITOR HAVING A POLYMER INTERNAL REFLECTIVE ELEMENT

(76) Inventor: Paul A. Wilks, Jr., 179 Middlesex Rd., Darien, CT (US) 06820

( * ) Notice: Subject to any disclaimer, the term of this patent is extended or adjusted under 35 U.S.C. 154(b) by 100 days.

(21) Appl. No.: 09/837,749

(22) Filed: Apr. 18, 2001

(65) Prior Publication Data
US 2002/0154289 A1 Oct. 24, 2002

(51) Int. Cl.[7] .............................................. G01N 33/28
(52) U.S. Cl. ........................................ 356/70; 356/436
(58) Field of Search ........................... 356/70, 436, 442, 356/128, 136

(56) References Cited

U.S. PATENT DOCUMENTS

| 1,940,772 A | | 12/1933 | Schoenberg ................... 88/14 |
|---|---|---|---|
| 2,889,736 A | | 6/1959 | Borg ............................ 88/14 |
| 3,049,964 A | | 8/1962 | Miller et al. .................. 88/14 |
| 3,578,865 A | | 5/1971 | Traver ......................... 356/70 |
| 4,345,202 A | | 8/1982 | Nagy et al. ............. 324/58.5 B |
| 4,422,714 A | * | 12/1983 | Benoit et al. ............... 356/136 |
| 4,495,417 A | | 1/1985 | Hohensang ................ 250/343 |
| 4,699,509 A | | 10/1987 | Kamiya et al. ............... 356/70 |
| 4,730,882 A | | 3/1988 | Messerschmidt |
| 4,829,186 A | * | 5/1989 | McLachlan et al. .......... 356/51 |
| 4,912,319 A | * | 3/1990 | Miyata et al. .............. 356/136 |
| 4,974,552 A | * | 12/1990 | Sickafus ..................... 356/128 |
| 4,975,581 A | | 12/1990 | Robinson et al. |
| 4,998,022 A | * | 3/1991 | Tregay ....................... 356/136 |
| 5,049,742 A | | 9/1991 | Hosonuma et al. ......... 250/301 |
| 5,159,199 A | | 10/1992 | LaBaw |
| 5,166,755 A | | 11/1992 | Gat |
| 5,170,056 A | * | 12/1992 | Berard et al. ............. 250/341.2 |
| 5,172,182 A | | 12/1992 | Sting et al. ................. 356/244 |
| 5,185,640 A | | 2/1993 | Wilks, Jr. et al. ........... 356/300 |
| 5,200,609 A | * | 4/1993 | Sting et al. .................. 250/226 |
| 5,223,142 A | * | 6/1993 | Kolbert ...................... 356/136 |
| 5,225,679 A | | 7/1993 | Clarke et al. ............... 250/343 |
| 5,309,213 A | | 5/1994 | Desjardins et al. ........... 356/70 |
| 5,442,435 A | * | 8/1995 | Cooper et al. ............. 356/133 |
| 5,452,083 A | | 9/1995 | Wilks, Jr. ................... 356/300 |
| 5,459,316 A | | 10/1995 | Doyle ..................... 250/339.11 |

(List continued on next page.)

FOREIGN PATENT DOCUMENTS

JP 2-249950 A 10/1990

OTHER PUBLICATIONS

"Hybrid Pyroelectric Linear Array With 128 Responsive elements And Integrated CMOS Multiplexer," DIAS Agnewandte Senorik GmbH, 5/99.
"Infrared In The Real World—How It Will Evolve In The New Millenium," Paul A. Wilks, Jr., Spectroscopy, Dec. 1999.

Primary Examiner—Michael P. Stafira
Assistant Examiner—Juan D Valentin, II
(74) Attorney, Agent, or Firm—Ohlandt, Greeley, Ruggiero & Perle, L.L.P.

(57) ABSTRACT

A detector assembly which is capable of analyzing a material, the detector assembly comprising: an internal reflection element which is formed of a polymer having internally reflecting surfaces and an optical index of refraction greater than that of the material; a base portion disposed substantially adjacent to the internal reflection element; a light source disposed within the base portion wherein it is in communication with the internal reflection element such that the light source is capable of radiating light into the internal reflection element such that it contacts the internally reflecting surfaces; and a light analyzer disposed within the base portion wherein it is in communication with the internal reflection element such that the light analyzer is capable of measuring the absorbance by the material as the light is discharged from the internal reflection element.

14 Claims, 1 Drawing Sheet

U.S. PATENT DOCUMENTS

| | | | |
|---|---|---|---|
| 5,483,335 A | | 1/1996 | Tobias |
| 5,548,393 A | * | 8/1996 | Nozawa et al. ............... 356/70 |
| 5,715,046 A | | 2/1998 | Tolvanen et al. ............. 356/70 |
| 5,724,151 A | * | 3/1998 | Ryley et al. ................ 356/432 |
| 5,730,366 A | * | 3/1998 | DeWitt ....................... 239/242 |
| 5,731,581 A | | 3/1998 | Fischer et al. |
| 5,742,064 A | | 4/1998 | Infante ................... 250/458.1 |
| 5,831,743 A | * | 11/1998 | Ramos et al. ............... 356/445 |
| 5,920,069 A | | 7/1999 | Fischer et al. |
| 5,946,084 A | * | 8/1999 | Kubulins .................... 356/128 |
| 5,991,029 A | * | 11/1999 | Doyle ........................ 356/451 |
| 6,061,139 A | * | 5/2000 | Takezawa et al. ............ 356/70 |
| 6,097,479 A | * | 8/2000 | Melendez et al. .......... 356/136 |
| 6,118,520 A | * | 9/2000 | Harner ........................ 356/73 |
| 6,205,272 B1 | | 3/2001 | O'Rourke et al. ............ 385/33 |
| 6,466,323 B1 | * | 10/2002 | Anderson et al. ........... 356/445 |
| 6,535,283 B1 | * | 3/2003 | Heffels et al. .............. 356/300 |

* cited by examiner

MONITOR HAVING A POLYMER INTERNAL REFLECTIVE ELEMENT

BACKGROUND OF THE INVENTION

1. Field of the Invention

The present invention relates to a monitor for detecting an absorbent within a fluid stream or stationary liquid. Moreover, the present invention relates to a low cost, easy to manufacture monitor having a polymer internal reflective element for detecting an absorbent in a fluid, such as carbon in engine oil.

2. Description of the Prior Art

The present invention makes use of radiant energy (hereinafter referred to as "light") technology to detect an absorbent within a fluid stream or stationary liquid, such as carbon or soot (hereinafter carbon) in engine oil.

Carbon is a natural occurrence in engine oil and exhaust emissions, resulting from incomplete combustion of fuel. This is especially true of diesel engines. The presence of carbon at elevated levels in the oil can be detrimental to the continued operation of the engine. The carbon present in the engine oil is maintained in suspension by the dispersant additives of the lubricant. As carbon levels increase, the viscosity of the oil also increases, putting added stress on engine components. Engine oils with high levels of suspended carbon can become abrasive, and can result in wear in areas of high load. Also, at higher levels of suspended carbon, the carbon may exceed the capacity of the dispersant additive, causing the carbon to deposit in critical oil ways, and in the oil filter—eventually leading to clogging of the oil ways and plugging of the filter. An accurate measurement of carbon, on a regular basis, is essential for minimizing the impact of this undesirable wear, as an indicator of oil condition and as an indicator of engine performance.

Recently promulgated regulations by the Environmental Protection Agency (EPA) require the virtual elimination of carbon from the exhaust emissions of diesel powered vehicles. The required filtering that enables diesel exhausts to meet these requirements results in a more rapid building of carbon in the engine lubricating oil, thus further increasing the need for a regular and accurate measurement of carbon. Additionally, EPA has promulgated regulations to reduce the production of other exhaust gasses, such as NOX. The implementation of the engine controls to necessary to reduce such emissions actually increases the production of carbon, further increasing the build-up of carbon in the engine oil.

Since excessive carbon in the oil can damage the engine, frequent oil changes are often used to prevent this type of engine damage. On the other hand, diesel engines contain several gallons of expensive lubricating oil, hence it is economically desirable not to change oil before it is necessary.

Therefore, its is desired to monitor the carbon content in the engine oil in order to minimize the potential for engine damage, detect failures, and minimize the frequency of oil changes.

Over the past 30 years several tests have been proposed and adopted for the measurement of suspended carbon in used diesel engine oils.

One such method, the blotter test, involves placing a drop of oil on a sheet of filter paper, and visually assessing the spot that is produced after the oil fully impregnates the paper. While this method is inexpensive and easy to use, the interpretation of the results is completely subjective.

Another method, the total solids procedure, involves mixing a measured quantity of oil with a suitable solvent—often heptane or a mixture of heptane and a polar solvent. The insoluble material is separated by centrifuging, and the separated solids are determined by weight. The total insolubles method is non-specific and may be a poor indicator for carbon if other materials are present. Moreover, it requires the use of volatile solvents, laboratory equipment and trained personnel. Further, the results of analysis using this laboratory based procedure, may not be available to the vehicle operator for several days after the submission of a sample and can often be quite expensive on a per test basis.

The recognized standard laboratory test procedure for dispersed carbon is thermo-gravimetric analysis TGA. It involves removing the volatile organic components by heating under a stream of inert gas and then eliminating the residual carbon in a stream of oxygen. The weight loss associated with the removal of carbon is measured. TGA tends to be the standard method of choice and is the only direct measurement of carbon as elemental carbon. But, similar to the total solids procedure, the results of analysis using this laboratory based procedure may not be available to the vehicle operator for several days after the submission of a sample and can often be quite expensive on a per test basis. TGA is often used as a calibration standard for the total solids and optical methods described herein.

Optical methods, especially infrared spectrometric analysis IR/FTm, involve the measurement of the attenuation of light visible or infrared by the carbon in the oil. The greater the carbon content, the greater the level of attenuation. This in turn can be correlated with carbon content. Instruments that measure the carbon level in engine oil using infrared absorption have been available for some time. But, similar to the total solids procedure and TGA analysis, the results of analysis using this laboratory based procedure may not be available to the vehicle operator for several days after the submission of a sample and can often be quite expensive on a per test basis.

Several field based testing devices utilizing the above referenced laboratory based methods are available. These devices reduce the time necessary to obtain the required results but also require complex operating, cleaning and calibration procedures which are required for accurate measurements and that can be difficult to follow in a field based environment.

Sensors making use of the principle of attenuated total reflection described above also are being developed for direct insertion into the oil passages of diesel engines. Such prior art devices are described in U.S. Provisional Application Serial No. 60/188,508 and U.S. Pat. No. 5,452,083 that are incorporated in their entirety herein. Such devices include a metal body having an infrared transmitting crystal, a source of infrared radiation and a detector that measures the attenuation of the radiation as it passed through the crystal in contact with the carbon containing oil. Such sensors are relatively expensive because of the costly crystal needed. Additionally, expensive machined metal parts and expensive detectors that detect the specific wavelength of carbon are required.

It is therefore desirable to have an inexpensive and easy to manufacture carbon monitor, which is capable of continuously monitoring the engine oil and can provide the operator with an instant warning when the carbon concentration has reached a dangerous level.

SUMMARY OF THE INVENTION

A detector assembly which is capable of analyzing a material, the detector assembly comprising: an internal reflection element which is formed of a polymer having internally reflecting surfaces and an optical index of refraction greater than that of the material; a base portion disposed substantially adjacent to the internal reflection element; a light source disposed within the base portion wherein it is in communication with the internal reflection element such that the light source is capable of radiating light into the internal reflection element such that it contacts the internally reflecting surfaces; and a light analyzer disposed within the base portion wherein it is in communication with the internal reflection element such that the light analyzer is capable of measuring the absorbance of the material as the light is discharged from the internal reflection element.

In order for the internal reflection element to function in the presence of oil it must have an optical index of refraction greater than that of lubricating oil which is approximately 1.4. Additionally, the internal reflection element must be capable of withstanding the operating temperature and the chemicals present in lubrication oils. The family of polyether-sulfones, amongst others, meets these requirements.

It is a further object of the present invention to provide a monitor for detecting carbon in the oil of an engine, wherein carbon is a universal absorber. The monitor has a light source, a light detector, a controller, and an internal reflection element. The internal reflection element has at least one internally reflecting surface adapted to be exposed to the oil and a connecting portion for connecting the internal reflection element to the engine.

It is yet another object of the present invention to provide a method of detecting carbon in the oil of an engine, wherein carbon is a universal absorber. The method has the steps of (1) exposing at least one internally reflecting surface of an internal reflection element to the oil, (2) controlling a light source to radiate light into the internal element at greater than the critical angle such that the light is internally reflected by the at least one internally reflecting surface, and such that an absorbed portion of the light is absorbed by the absorbent through the at least one internally reflecting surface and a remaining portion of the light is radiated from the internal reflection element at less than the critical angle, and (3) controlling a light detector to detect the remaining portion of the light, wherein the internal reflection element includes the source and the detector operatively positioned therein and has an optical index of refraction greater than that of the oil.

DETAILED DESCRIPTION OF THE PREFERRED EMBODIMENT

Figure 1:
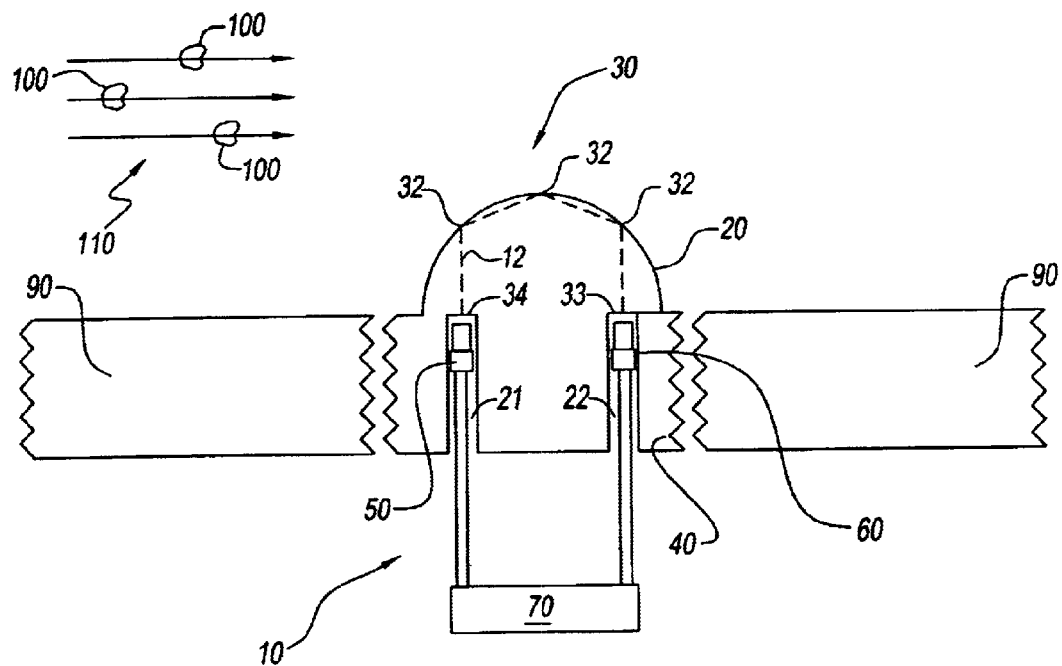
FIG. 1 is a cross sectional view of a monitor according to the present invention.
Figure 2:
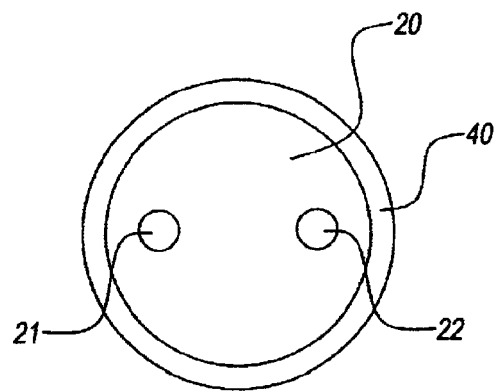
FIG. 2 is a bottom view of the monitor of FIG. 1.

The monitor 10 of the present invention is shown in FIGS. 1 and 2. Monitor 10 is preferably disposed in a wall 90 of, for example, an internal combustion or diesel engine, to detect the concentration of an absorbent 100 within a fluid 110. Absorbent 100 is suspended, dissolved or otherwise in (hereinafter in) fluid 110. Fluid 110 may be a fluid stream, a stationary liquid. For example, in a preferred embodiment of the present invention, wall 90 is a diesel engine, absorbent 100 is carbon, and fluid 110 is engine oil.

The present invention is adapted for use with absorbents 100, for example, carbon. More specifically, in the present invention absorbent 100 absorbs light at all wavelengths. The present invention also utilizes attenuated total reflection. Thus, monitor 10 is adapted to radiate light into an internal reflective element in contact with the absorbent 100 and to detect the portion of the light that is not absorbed by the absorbent. The variance between the amount of light radiated into monitor 10 and the amount of light detected by the monitor is proportional to the concentration of the absorbent in contact with the monitor. Accordingly, monitor 10 is adapted to detect the concentration of absorbent 100 in fluid 110.

Shown in FIG. 1, monitor 10 has an internal reflection element 20, a light source 50, a light detector 60, and a controller 70. It should be recognized that internal reflection element 20 is shown by way of example as hemispherical. However, it is considered within the scope of the present invention for internal reflection element 20 to be of any known configuration. Light source 50 and light detector 60 are operatively positioned in internal reflection element 20. In a preferred embodiment, internal reflection element 20 includes a hole 21 having light source 50 and a hole 22 having detector 60 operatively positioned therein. Hole 21 includes surface 34 and hole 22 includes surface 33. Surface 34 is adapted to allow light 12 to enter internal reflection element 20, and surface 33 is adapted to allow light 12 to exit the internal reflection element. Thus, light 12 from light source 50 is radiated into internal reflection element 20 at surface 34 at less than the critical angle. Light 12 is internally reflected and is absorbed by absorbent 100 at one or more internally reflecting surfaces 32, at greater than the critical angle. Light 12 passes out of internal reflection element 20 when it reaches surface 33 at less than the critical angle. Light 12 at the wavelength of normal absorption for absorbent 100 is absorbed by the absorbent through internally reflecting surfaces 32.

Controller 70 is operatively coupled with light source 50 and light detector 60. In a first embodiment, controller 70 is connected to monitor 10. Alternately, controller 70 is remote from monitor 10. Thus, monitor 10 controls light source 50 to radiate light 12 into internal reflection element 20 and controls light detector 60 to detect the light as it passes out of the internal reflection element. The variance between the total amount of light radiated into monitor 10 by light source 50 and the amount of light exiting the monitor at detector 60 is proportional to the concentration of absorbent 100 in contact with the monitor. Source 50 is a source such as, but not limited to an incandescent light source, a light emitting diode, laser, and the like. In a preferred embodiment, source 50 is an incandescent light. Preferably, detector 60 is a broad-spectrum detector, such as, but not limited to, a photocell, a photo-multiplier tube, pyro-electric detector and the like.

Monitor 10 is adapted to be connected to wall 90 such that internal reflection element 20 is exposed to fluid 110 having absorbent 100. Preferably, internal reflection element 20 has a connecting portion 40 for connecting the internal reflection element to wall 90. Connecting portion 40, shown in FIG. 1, is preferably threaded to secure monitor 10 to wall 90. However, any suitable means of securing monitor 10 to wall 90 such that internal reflection element 20 is exposed to absorbent 100 is considered within the scope of the present invention. Thus, connection portion 40 includes, but is not limited to, mechanical connecting, adhesive connecting, bonding, and the like.

Preferably, internal reflection element 20 is a unitary device 30. Moreover, internal reflection element 20 is made of a polymer material that has an optical index of refraction greater than that of fluid 110; is insoluble in the fluid; can withstand the operating conditions to which the internal reflection element is exposed; and is moldable to most any conventional shape. Internal reflection element 20 is preferably molded or machined. In a preferred embodiment, internal reflection element 20 is molded of a polymer selected from the group consisting of polyether-sulfone.

Accordingly, monitor 10 provides a low cost device by eliminating the need for costly infrared crystals, eliminating the need for all machining operations, reducing the assembly requirements and permitting the use of low cost light sources 50 and light detectors 60. More specifically, in the preferred embodiment monitor 10 is a low cost device having a molded polyether-sulfone internal reflection element 20, an incandescent light source 50 and a broad spectrum detector 60.

It should be understood that the foregoing description is only illustrative of the invention. Various alternatives and modifications can be devised by those skilled in the art without departing from the invention. Accordingly, the present invention is intended to embrace all such alternatives, modifications and variances that fall within the scope of the appended claims.

What is claimed is:

1. A detector assembly which is capable of analyzing at least one material, said detector assembly comprising:
   an internal reflection element which is formed of a polymer having internally reflecting surfaces and an optical index of refraction greater than that of said material;
   a base portion is integrally formed with said internal reflection element from said polymer to form a unitary device;
   a light source disposed within said base portion wherein it is in communication with said internal reflection element such that said light source is capable of radiating light into said internal reflection element such that it contacts said internally reflecting surfaces; and
   a light analyzer disposed within said base portion wherein it is in communication with said internal reflection element such that said light analyzer is capable of measuring the absorbance of said material as said light is discharged from said internal reflection element.

2. The detector of claim 1, wherein said polymer is selected from the group consisting of polyether-sulfone and other high index of refraction materials.

3. The detector of claim 1, wherein said unitary device is provided by molding or machining.

4. The detector of claim 1, wherein said polymer internal reflection element has a hemispherical shape.

5. The detector of claim 1, wherein said base portion comprises a connecting portion for mounting the detector in a desired location, said connecting portion being selected from the group consisting of: a mechanical connection, an adhesive connection, and a bonding connection.

6. A monitor for detecting at least one material contained in a mixture, said monitor comprising:
   a controller; and
   detector assembly which is capable of analyzing said material, said detector assembly comprising: an internal reflection element which is formed of polyether-sulfone having internally reflecting surfaces and an optical index of refraction greater than that of said material; a base portion formed as part of said internal reflection element from said polyether-sulfone; a light source disposed within said base portion wherein it is in communication with said internal reflection element such that said light source is capable of radiating light into said internal reflection element such that it contacts said internally reflecting surfaces; and a light analyzer disposed within said base portion wherein it is in communication with said internal reflection element such that said light analyzer is capable of measuring the absorbance of said material as said light is discharged from said internal reflection element,
   wherein said controller controls said light source to radiate light into said internal reflection element at greater tan the critical angle such that said light is reflected on said internally reflection surface, a portion of said light is absorbed by said material, wherein said non-absorbed portion of said light is discharged from said internal reflective element at less than the critical angle, and causes said light analyzer to measurer the absorbed light.

7. The monitor of claim 6, wherein said light source is selected from the group consisting of: an incandescent light source, a light emitting diode and a laser.

8. The monitor of claim 6, wherein said light detector is a broad-spectrum detector.

9. The monitor of claim 6, wherein said internal reflection element has a hemispherical shape.

10. The monitor of claim 6, wherein said light detector has a predetermined wavelength.

11. A detector element comprising:
    an internal reflection portion;
    a base portion for mounting the detector element in a desired location so that said internal reflection portion is exposed to a target material;
    a first hole formed in said base portion, said first hole receiving a light source therein; and
    a second hole formed in said base portion, said second hole receiving a light detector therein, said first and second holes being positioned in said based portion so that light radiated from said light source into said internal reflection portion at said first hole is internally reflected within said internal reflection portion before exiting said internal reflection portion at said second hole into said light detector, wherein said internal reflection portion and said base portion are formed as a unitary element of polymeric material having a selected optical index of refraction.

12. The detector element as in claim 11, wherein said base portion has a threaded section for mounting the detector element in said desired location.

13. The detector element as in claim 11, wherein said internal reflection portion has a hemispherical shape.

14. The detector element as in claim 11, wherein said polymeric material is polyether-sulfone.

* * * * *